United States Patent [19]
Monroe et al.

[11] Patent Number: 5,527,262
[45] Date of Patent: Jun. 18, 1996

[54] HAND-HELD DIAGNOSTIC DENTAL PROBE WITH VIDEO IMAGING

[75] Inventors: Richard A. Monroe, Liverpool; Robert J. Wood, Syracuse; Gregory E. Pasik, Auburn; Robert R. Huntley, Skaneateles Falls, all of N.Y.

[73] Assignee: Welch Allyn, Inc., Skaneateles Falls, N.Y.

[21] Appl. No.: 531,889

[22] Filed: Sep. 22, 1995

Related U.S. Application Data

[63] Continuation of Ser. No. 292,712, Aug. 18, 1994, abandoned.

[51] Int. Cl.$^6$ ..................................................... A61B 1/04
[52] U.S. Cl. ........................ 600/110; 600/130; 600/163; 348/66; 433/29
[58] Field of Search ..................................... 600/101, 109, 600/110, 112, 129, 130, 160, 162, 163, 172, 176, 178, 179; 348/65, 66, 77; 433/29

[56] References Cited

U.S. PATENT DOCUMENTS

| | | | |
|---|---|---|---|
| 4,604,992 | 8/1986 | Sato | 128/6 |
| 4,727,416 | 2/1988 | Cooper et al. | 600/129 |
| 4,919,114 | 4/1990 | Miyazaki | 600/110 |
| 4,969,450 | 11/1990 | Chinnock et al. | 128/6 |
| 5,016,098 | 5/1991 | Cooper et al. | 600/129 |
| 5,051,823 | 9/1991 | Cooper et al. | 600/129 |
| 5,051,824 | 9/1991 | Nishigaki | 358/98 |
| 5,079,629 | 1/1992 | Oz | 348/77 |
| 5,239,984 | 8/1993 | Cane et al. | 128/9 |
| 5,251,025 | 10/1993 | Cooper et al. | 128/6 |
| 5,363,135 | 11/1994 | Inglese | 433/29 |
| 5,363,839 | 11/1994 | Lankford | 128/6 |
| 5,408,992 | 4/1995 | Hamlin et al. | 600/109 |
| 5,427,087 | 6/1995 | Ito et al. | 600/109 |
| 5,429,119 | 7/1995 | Griffin et al. | 600/200 |

OTHER PUBLICATIONS

Hovnanian et al., "An Electro–Optic Dental Monitor," NEREM RECORD, 1959 Northeast Electronics Research and Engineering Meeting.

Primary Examiner—Angela D. Sykes
Assistant Examiner—Eric F. Winakur
Attorney, Agent, or Firm—Harris Beach & Wilcox

[57] ABSTRACT

An improved hand-held diagnostic dental probe includes a casing that having a hand-holdable body portion, a neck portion that extends from the body portion to a head portion that is formed of a back cover and a front cover. A circuit board assembly in the body portion contains video processing circuitry, and a flexible neck board extends forward from the body portion through the neck portion of the casing to a head board located in the head portion of the casing. A solid state imager and a miniature lamp are disposed on the head board. The front cover contains an adjustable focus lens cell for focusing on the imager an image of a target in the lens cell's field of view. The instrument provides a monitor-ready standard format full color video signal.

9 Claims, 2 Drawing Sheets

5,527,262

HAND-HELD DIAGNOSTIC DENTAL PROBE WITH VIDEO IMAGING

This is a Continuation of Application No. 08/292,712 filed Aug. 18, 1994, now abandoned.

BACKGROUND OF THE INVENTION

1. Field of the Invention

This invention relates to hand-held diagnostic instruments for either clinical or industrial use, and is specifically directed to a device that employs a miniature video camera and a self-contained light source. The instrument of the present invention can be a video probe, a video otoscope, a nasal scope, an epidural scope, or any one of a number of other diagnostic scopes. The instrument can also be designed for particular industrial inspections as, for example, examination of recessed equipment parts.

2. Discussion of the Related Art

Miniature video cameras have recently been incorporated into a wide variety of diagnostic instruments for producing a video image of a concealed target. Such instruments include, for example, laparoscopes, endoscopes, and borescopes. These prior devices require a separate source of illumination, and a fiber optic conduit to carry the light forward to illuminate the target.

In addition to this known video technology used in association with these relatively large diagnostic instruments, a number of smaller diagnostic instruments exist for the direct examination of tissue so that a medical practitioner can diagnose the health of such tissue by inspection of a particular patient. These types of diagnostic instruments include, for example, otoscopes, epidural scopes, and dental mirrors. Such instruments, however, require the practitioner to place the practitioner's eye near or on the instrument to conduct an inspection of the subject target while an image of the inspected tissue remains solely as a mental impression within the practitioner's memory. It is impossible with these conventional instruments to create any sort of hard copy record or permanent image of the object or target under inspection.

OBJECTS AND SUMMARY OF THE INVENTION

Accordingly, it is a principal object of this invention to provide a hand-held diagnostic instrument which includes a miniature video imager, focusing optics, and a light source, as well as necessary electronic circuitry to produce a monitor-ready standard video signal, so that an inspector or practitioner can view a target on a standard video monitor.

It is another object of the present invention to provide a line of hand-held devices for different industrial and clinical purposes, the devices being generally common in style and function with a specific type of head cover.

A further object of this invention is to provide a hand-held instrument with adjustable focusing optics whose focal length can be changed manually such that a user of the instrument can hold the instrument and adjust its focus with one hand.

These and other objects are attained in accordance with the present invention wherein there is provided an improved hand-held diagnostic instrument with video imaging capability. According to one aspect of this invention, the hand-held diagnostic instrument is provided with a casing or housing that has a hand-holdable body portion, a neck portion that extends forward from one end of the body portion, and a head portion situated on the distal end of the neck portion. The head portion is comprised of a back cover and a front cover. An arrangement of circuit boards is fitted into the body portion of the casing and contains video processing circuitry. A circuit board and/or flexible circuit member extends from the body portion through the neck portion of the casing and provides a receptacle for a head member which is positioned in the head portion of the casing. A solid-state imager, such as a CCD chip, is carried in the head member and is connected with the video processing circuitry on the circuit boards. A focusing lens assembly is carried in the front cover and focuses onto the imager an image of an object in the field of view of the lens assembly. In one preferred embodiment, the lens assembly includes a manually actuable detenting mechanism for adjusting the focal length. A miniature lamp is carried on the head member displaced a small distance from the imager. The front cover is provided with a window or opening that directs illumination from the lamp into the field of view of the focusing lens assembly. A conduit or cable carries a processed standard format video signal to a monitor, and also carries power forward to the lamp, imager, and image processing circuitry. The picture on the monitor is an image of the target as viewed by the imager in the instrument. This picture can be digitized and captured, for example, for storage in a magnetic memory of a small computer. A hard or paper copy of the image can then be generated.

The head cover and neck of the device can be disinfected after a clinical use. Disposable transparent sterile sheaths can be employed to cover the head and neck to prevent contamination from a patient's body fluids. In addition, the front and back covers of the head portion can be detachable and interchangeable with covers of another style to convert the instrument, for example, from a nasal probe to an otoscope.

BRIEF DESCRIPTION OF THE DRAWING

Further objects of the present invention together with additional features contributing thereto and advantages accruing therefrom will be apparent from the following description of a preferred embodiment of the invention which is shown in the accompanying drawing, wherein.

DETAILED DESCRIPTION OF A PREFERRED EMBODIMENT

Figure 1:
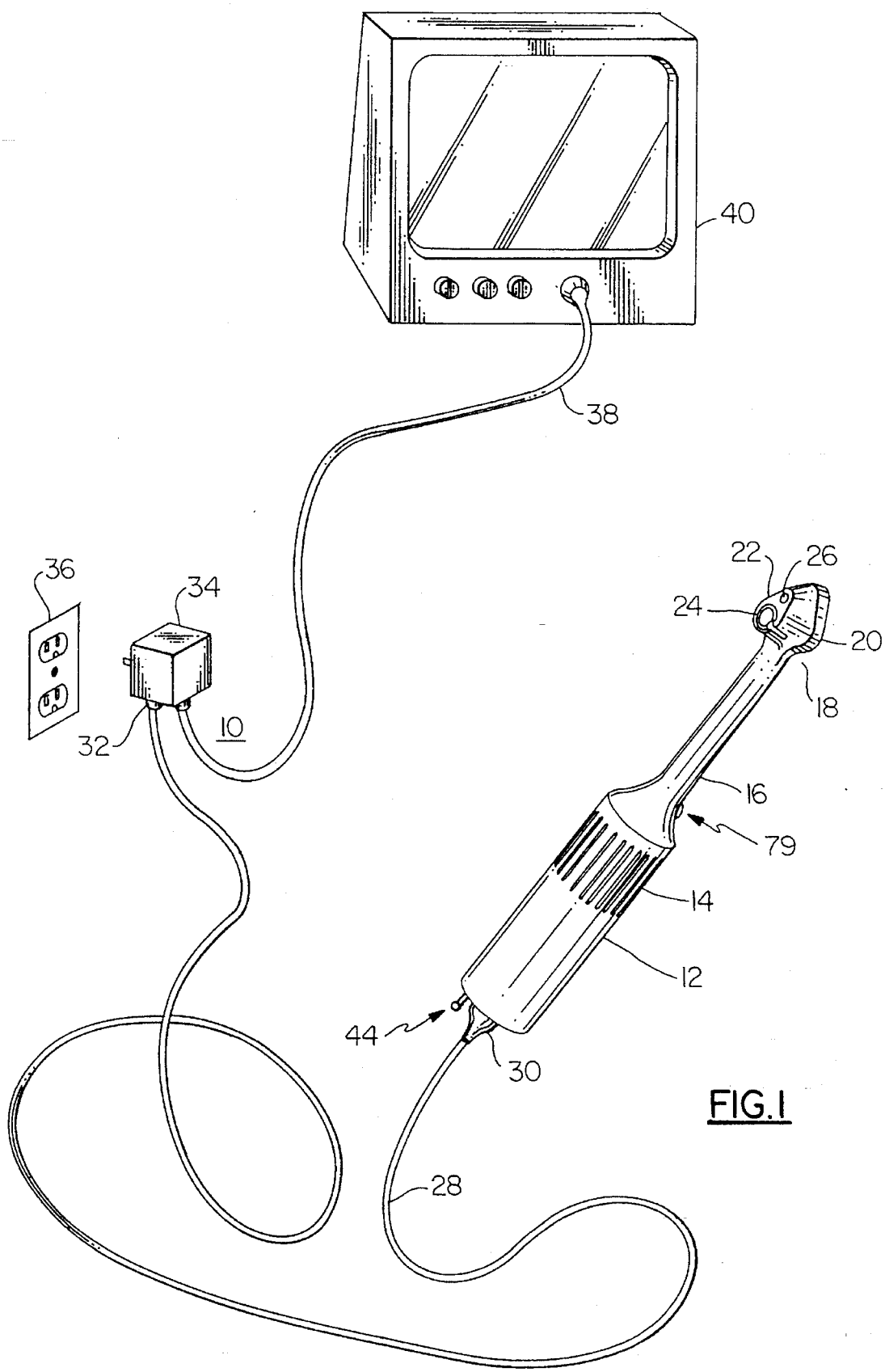
FIG. 1 is a perspective view of a hand-held multipurpose diagnostic instrument in combination with an associated power supply and monitor, the device of FIG. 1 being configured as a variable focus dental camera.

With reference to the Drawing, and initially to FIG. 1 a video dental camera 10 embodies the principles of this invention. The camera has a hand-holdable casing 12 with a generally cylindrical body portion 14, a narrow elongated neck portion 16 that extends from an upper end of the body portion 14, and a head portion 18. The head portion is somewhat oval in shape, and has a back cover 20 and a front cover 22. An adjustable lens cell 24 is situated on the head portion 18 in the front cover 22, and a lamp window 26 is provided on the cover 22 above the lens cell 24. Processed video signals are carried on a cable 28 that enters the body portion 14 through a strain relief 30, and which has a connector 32 that couples to a power supply box 34. As illustrated in FIG. 1, the power supply box 34 is of the type adapted to be plugged into a common wall outlet 36 connected to the mains. A video cable 38 couples a video monitor 40 to the cable 28 through a wiring harness (not shown) inside the power supply box 34.

Figure 2:
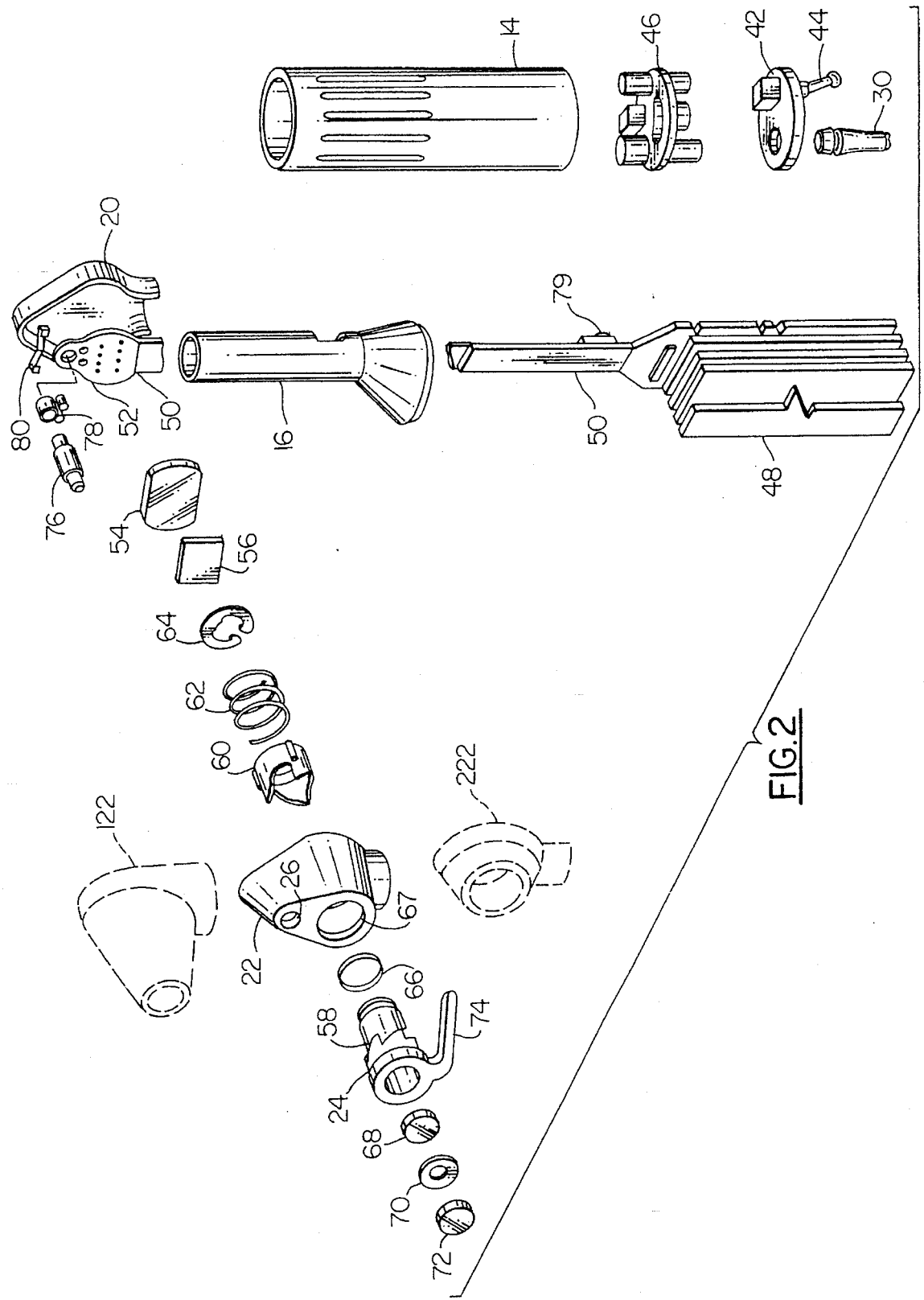
FIG. 2 is an exploded assembly view of the embodiment of the present device illustrated in FIG. 1, FIG. 2 also showing in phantom alternative otoscope and episcope head covers.

Details of the instrument 10 and a preferred way of adjusting the optics are shown in the exploded assembly view of FIG. 2. The body portion 14 of the shell is closed off at its lower end by an end cap 42 which seats the strain relief 30 and carries an on-off system switch 44, also shown in FIG. 1. The on-off system switch 44 is for activating or deactivating the entire scope system including the video monitor 40. An end printed circuit board 46 is in the form of a disk positioned just ahead of the end cap 42. A stack of circuit boards 48, located within the body portion 14, carries video processing circuitry. A flexible circuit board 50 carrying flexible circuitry extends longitudinally through the neck portion 16 of the casing and connects to a head board 52 which is contained within the head portion 18.

A miniature CCD imager chip 54 is mounted on the head board 52 with an infrared filter 56 positioned over the imager chip 54. The imager chip 54 is preferably detachable from the head board 52 of the flexible circuit board 50 so that the imager chip 54 may be replaced with a substitute CCD imager or another circuit element. This type of plug-in and removable CCD imager chip is currently available and well known in the prior art. The lens cell 24 is generally cylindrical and carries a detent member 58 which cooperates with a detent ring 60 that is fixed in an opening 67 in the front cover 22. The lens cell 24 is biased rearwards by a coil spring 62 that is retained between the detent ring 60 and a retaining ring 64 that mounts in a recess at the rear end of the cell 24. A ring seal 66 fits over the lens cell 24 and creates a fluid tight seal at the entry to an opening 67 in the front cover 22.

An objective lens 68, an aperture plate 70, and a plano lens 72 are disposed in the forward or distal end of the lens cell 24. A lever 74 protrudes laterally from the end of the lens cell 24, and then curves backward over the contour of the front cover 22, as shown in FIG. 1. To adjust the focus of the lens cell 24, the practitioner simply moves the lever 74 to rotate the lens cell. This mates a ramp surface of the detent member 58 with a corresponding ramp surface of the fixed detent ring 60. The axial position of the lens cell moves with rotations until the picture appearing on the monitor 40 is in focus. The focusing is achieved with one-hand operation, that is, the practitioner can move the lever 74 with the forefinger or thumb of the same hand used to hold the instrument. A miniature lamp 76 is fitted into a lampholder 78 mounted at one end of the head board 52. Activation of the lamp 76 is independently controlled by an on-off lamp switch 79. An electrical contact 80 fitted to the board 52 is spring biased against a contact on the lamp 76. The lamp is positioned to direct illumination forward through the window 26 in the front cover 22 and into the field of view of the lens cell 24. The front cover 22 can be removed when necessary, for example, to replace the lamp 76. Thereafter, the front cover easily snaps back in place on the neck portion 16 and back cover 20.

The instrument shown here is a dental camera, and the front and rear covers 20 and 22 of the head portion are somewhat teardrop shaped. This shape is convenient for placing in a dental patient's mouth to permit the dentist to see the patient's teeth and gums on the monitor 40. The instrument, however, can be easily configured as another hand-held instrument simply by installing a different front cover and back cover. Here, as shown in phantom, an otoscope front cover 122 has a conic nose, while an alternate front cover 222 for an episcope has a flattened frustoconic nose. Each of the alternative covers has a corresponding rear cover (not shown) and focusing optics. The focusing optics can either be adjustable or fixed. In addition, the alternative front covers 122 and 222 also include means for directing light from the lamp 76 forward into the field of view of the associated focusing optics. This illumination may be supplied directly from a lamp or through a fiber bundle, or indirectly by use of a reflector.

A disposable sanitary sheath or cover can be placed over the neck and head portions 16 and 18 to prevent a patient's body fluids from contacting and contaminating the instrument. The sheath is optically transparent at least on the portion that overlies the front cover 22. In addition, the various alternative configurations have focusing lens assemblies of a viewing angle and aperture as needed for a specific application. Each of the various configurations, however, employs a common CCD imager and a common electrical circuit. The image processing circuitry preferably converts raw video information from the imager chips 54 into a monitor ready standard format signal suitable for the particular monitor 40. This can be a standard NTSC, PAL, or Secam color video signal, for example.

While this invention has been described in detail with reference to a certain preferred embodiment and alternative head cover configurations, it should be appreciated that the present invention is not limited to that precise embodiment or particular cover configurations. Rather, in view of the present disclosure which describes the current best mode for practicing the invention, many modifications and variations would present themselves to those of skill in the art without departing from the scope and spirit of this invention, as defined in the following claims.

What is claimed is:

1. An improved hand-held diagnostic dental probe comprising:

a casing including a hand-holdable body portion, a neck portion extending distally from the body portion, and a head portion formed with a front cover and a back cover;

circuit board means within said casing including video processing circuitry, said circuit board means further including a flexible board extending from said body portion through said neck portion of said casing and having a head member positioned in the head portion of said casing;

a solid state imager affixed to said head member and in circuit communication with said video processing circuitry;

focusing means carried on said front cover for focusing onto the imager an image of a target object or area in its field of view;

a lamp carried on said head member;

means in said front cover for directing illumination from said lamp into said field of view;

and conduit means for carrying power to said video processing circuitry and to said lamp, and for carrying from said video processing circuitry a video signal representing said target object or area in said field of view, said focusing means including an adjustable lens cell that is manually actuable to adjust its focal length thereby providing said solid state imager with a variable field of view.

2. The hand-held diagnostic dental probe according to claim 1 wherein said lens cell has a cylindrical ramp member that mates with a rotationally fixed cylindrical ramp in said front cover, and manual lever means for rotating said lens cell to move the ramp member and cylindrical ramp axially with respect to one another.

3. The hand-held diagnostic dental probe according to claim 1 wherein said video processing circuitry on said circuit board means outputs to said conduit means a standard monitor-ready full color video signal.

4. The hand-held diagnostic dental probe according to claim 1 further including a monitor connected to said conduit means, said monitor capable of displaying a video image of said target object or area.

5. The hand-held diagnostic dental probe according to claim 1 further including a power supply connected to said conduit means, said power supply being remotely located from said casing so that the dental probe is light-weight and easily manipulated around a patient's oral cavity.

6. An improved hand-held diagnostic dental probe comprising:

a casing including a hand-holdable body portion, a neck portion extending distally from the body portion, and a head portion;

circuit board means within said casing including video processing circuitry, said circuit board means further including a flexible board extending from said body portion through said neck portion of said casing and having a head member positioned in said head portion of said casing;

a solid state imager affixed to said head member and in circuit communication with said video processing circuitry;

a lamp within said head member for illuminating a target object or area;

means in said head portion for directing illumination from said lamp into said field of view;

focusing means on said head portion for focusing onto the imager an image of said target object or area positioned within said solid state imager's field of view; and conduit means for carrying power to said video processing circuitry and to said lamp, and for carrying from said video processing circuitry a video signal representing said target object or area in said field of view, said focusing means including an adjustable lens cell that is manually actuable to adjust its focal length thereby providing said solid state imager with a variable field of view.

7. The hand-held diagnostic dental probe according to claim 6 wherein said lens cell has a cylindrical ramp member that mates with a rotationally fixed cylindrical ramp in said head portion, and manual lever means for rotating said lens cell to move the ramp member and cylindrical ramp axially with respect to one another.

8. The hand-held diagnostic dental probe according to claim 6 further including a monitor connected to said conduit means, said monitor capable of displaying a video image of said target object or area.

9. The hand-held diagnostic dental probe according to claim 6 further including a power supply connected to said conduit means, said power supply being remotely located from said casing so that the dental probe is light-weight and easily manipulated around a patient's oral cavity.

* * * * *